United States Patent [19]

Kishino et al.

[11] 4,150,155
[45] Apr. 17, 1979

[54] PESTICIDALLY ACTIVE O,S-DIALKYL-N-SUBSTITUTED-N-SULFONYL-PHOSPHORAMIDOTHIOLATES

[75] Inventors: Shigeo Kishino; Junichi Saito; Akio Kudamatsu; Kozo Shiokawa; Shinichi Tsuboi, all of Tokyo, Japan

[73] Assignee: Nihon Tokushu Noyaku Seizo K.K., Tokyo, Japan

[21] Appl. No.: 834,862

[22] Filed: Sep. 19, 1977

[30] Foreign Application Priority Data

Sep. 20, 1976 [JP] Japan ................................ 51-111746

[51] Int. Cl.² ............................ A01N 9/36; C07F 9/24
[52] U.S. Cl. ...................................... 424/216; 260/947
[58] Field of Search ......................... 260/947; 424/216

[56] References Cited

U.S. PATENT DOCUMENTS 3,716,600  2/1973  Magee ............................. 260/947 X

FOREIGN PATENT DOCUMENTS 833863  5/1960  United Kingdom ..................... 260/947

OTHER PUBLICATIONS

Russian Zh. Obsch Khim 36 (5) 930, p. 25, line 21.

*Primary Examiner*—Anton H. Sutto
*Attorney, Agent, or Firm*—Sprung, Felfe, Horn, Lynch & Kramer

[57] ABSTRACT

O,S-Dialkyl-N-substituted N-sulfonyl-phosphoramidothiolates of the formula

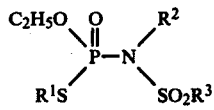

in which
$R^1$ is ethyl, n-butyl or sec.-butyl,
$R^2$ is alkyl with 1-6 carbon atoms, alkenyl with 2-6 carbon atoms, phenyl, or phenyl substituted with up to two substituents selected from the group consisting of halogen and akyl with 1-6 carbon atoms, and
$R^3$ is alkyl or halogen-substituted alkyl with 1-6 carbon atoms, aralkyl, phenyl or phenyl substituted with up to two substituents selected from the group consisting of halogen, alkyl with 1-6 carbon atoms and nitro, which possess insecticidal, acaricidal and nematicidal properties.

12 Claims, No Drawings

PESTICIDALLY ACTIVE O,S-DIALKYL-N-SUBSTITUTED-N-SULFONYL-PHOSPHORAMIDOTHIOLATES

The present invention relates to and has for its objects the provision of particular new O,S-dialkyl-N-substituted-N-sulfonyl-phosphoramidothiolates which possess insecticidal, acaricidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

U.S. Pat. No. 3,716,600 discloses that a wide variety of compounds of the general formula

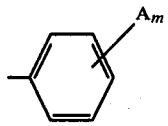
(VIII)

in which
R represents an alkyl group having 1 to 3 carbon atoms,
R' represents an aliphatic group having 1 to 3 carbon atoms,
R'' represents an alkyl group having 1 to 10 carbon atoms, a cycloalkyl group having 3 to 8 carbon atoms or a phenyl group, and
Y represents an oxygen or sulfur atom,
have insecticidal and acaricidal activities.

Hitherto, Parathion has been widely used as an insecticide, for example for controlling rice borers, planthoppers and leafhoppers which are important insects that are harmful to rice. The use of Parathion, however, has been suspended in some areas, particularly in Japan, because despite its excellent effectiveness against the pests, there is considered to be a great danger of its causing acute toxicity to mammals.

Furthermore the long-term use of large amounts of organophosphorus compounds, such as parathion, EPN, BAYCID and Sumithion, organochlorine compounds, such as BHC and DDT, and carbamate compounds, such as Sevin, has resulted in the pests attaining resistance to these chemicals.

Hence there is a need for new pesticides which have only a low toxicity to warm-blooded animals but which are effective against those pests that have attained resistance to prior-art pesticides.

The present invention now provides, as new compounds, the phosphoric acid amide esters of the general formula

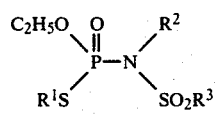
(I)

in which
$R^1$ is ethyl, n-butyl or sec.-butyl,
$R^2$ is alkyl with 1–6 carbon atoms, alkenyl with 2–6 carbon atoms or a group of the general formula

wherein
A is halogen or alkyl with 1–6 carbon atoms, and
m is 0, 1 or 2, and
$R^3$ is alkyl with 1–6 carbon atoms, which may be substituted by halogen, or is aralkyl or a group of the general formula

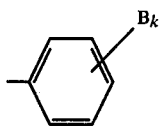

wherein
B is halogen, alkyl with 1–6 carbon atoms or nitro, and
k is 0, 1 or 2.

It has been found that compounds of the formula (I) exhibit unusually strong insecticidal, acaricidal and nematicidal activities, and possess a high effectiveness and a wider controlling effect than compounds of the formula (VIII); particularly, they have an excellent activity against spider mites that have attained resistance to various known organophosphorus pesticides.

Preferably, in formula (I), $R^2$ represents $C_1$–$C_4$ alkyl, $C_2$–$C_4$ alkenyl (for example vinyl, allyl, propenyl or methallyl, allyl being especially preferred), unsubstituted phenyl or phenyl carrying one or two substituents selected from chlorine atoms and $C_1$–$C_4$ alkyl groups (especially methyl), and $R^3$ represents $C_1$–$C_4$ alkyl, halogenated $C_1$–$C_4$ alkyl (for example bromomethyl, 2-chloroethyl, 2-bromoethyl, 3-chloropropyl, 3-chlorobutyl, 4-chlorobutyl, 1-methyl-2-chloropropyl, 1-methyl-3-chloropropyl, 1-chloromethyl-ethyl, 1-chloromethyl-2-chloroethyl and, especially, chloromethyl), benzyl, 2-phenylethyl, unsubstituted phenyl or phenyl carrying one or two substituents selected from $C_1$–$C_4$ alkyl groups (especially methyl), halogen atoms and nitro groups.

The present invention also provides a process for the preparation of a compound of the formula (I) in which
(a) a phosphoramidothioate salt of the general formula

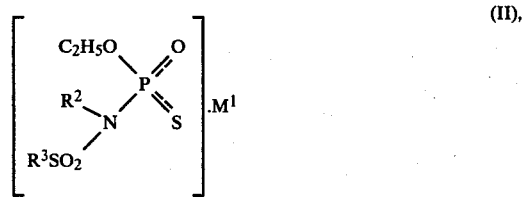
(II), in which
$R^2$ and $R^3$ have the meanings stated above, and
$M^1$ is an alkali metal atom (preferably sodium or potassium) or an ammonium group (for example, triethylammonium, dimethylammonium or pyridinium),
is reacted with an alkylating agent of the general formula $R^1 \cdot Y$ (III), in which
- $R^1$ has the meaning stated above and
- Y is a halogen atom or a sulfonic acid group (for example benzenesulfonate, p-toluenesulfonate, monoethylsulfonate, monobromosulfonate or monosec.-butylsulfate), or (b) a thiophosphoryl halide of the general formula $$\underset{R^1S}{\overset{C_2H_5O}{\diagdown}}\overset{O}{\underset{\|}{P}}-Hal \qquad (IV),$$

in which
- $R^1$ has the meaning stated above and
- Hal is halogen, preferably chlorine, is reacted with a sulfonylamide or sulfonylanilide salt of the general formula $$M^2-N\overset{R^2}{\underset{SO_2R^3}{\diagup}} \qquad (V),$$

in which
- $R^2$ and $R^3$ have the meanings stated above and
- $M^2$ is an alkali metal atom (preferably sodium or potassium).

The phosphoramidothioate salt (II) to be used in process variant (a) can be prepared by reacting a phosphoramidothioate of the general formula $$(C_2H_5O)_2\overset{S}{\underset{\|}{P}}-N\overset{R^2}{\underset{SO_2R^3}{\diagup}} \qquad (VI),$$

in which
- $R^2$ and $R^3$ have the meanings stated above, with a dealkylating agent of the general formula $$R^4SM^1 \qquad (VII),$$

in which
- $M^1$ has the meaning given above, and
- $R^4$ is hydrogen, alkyl (preferably with 1–4 carbon atoms) or alkoxythiocarbonyl (for example methoxythiocarbonyl or ethoxythiocarbonyl).

Specific examples of the phosphoramidothioate salts represented by the general formula (II) are: potassium O-ethyl-N-methyl-N-methanesulfonyl-phosphoramidothioate, potassium O-ethyl-N-methyl-N-butanesulfonylphosphoramidothioate, potassium O-ethyl-N-methyl-N-chloromethanesulfonylphosphoramidothioate, potassium O-ethyl-N-methyl-N-benzenesulfonyl-phosphoramidothioate, potassium O-ethyl-N-methyl-N-4-chlorobenzenesulfonylphosphoramidothioate, potassium O-ethyl-N-methyl-N-2,5-dichlorobenzenesulfonylphosphoramidothioate, potassium O-ethyl-N-methyl-N-2,5-dimethylbenzenesulfonylphosphoramidothioate, potassium O-ethyl-N-methyl-N-2-nitrobenzenesulfonylphosphoramidothioate, potassium O-ethyl-N-methyl-N-phenylmethanesulfonylphosphoramidothioate, potassium O-ethyl-N-iso-propyl-N-methanesulfonylphosphoramidothioate, potassium O-ethyl-N-allyl-N-methanesulfonylphosphoramidothioate, potassium O-ethyl-N-allyl-N-benzenesulfonylphosphoramidothioate, potassium O-ethyl-N-phenyl-N-methanesulfonylphosphoramidothioate, potassium O-ethyl-N-2-tolyl-N-methanesulfonylphosphoramidothioate, and potassium O-ethyl-N-chloro-2-tolyl-N-methanesulfonylphosphoramidothioate, and the corresponding sodium salts, triethylammonium salts, dimethylanilinium salts and pyridinium salts.

Specific examples of the alkylating agents of the general formula (III) are: ethyl-, butyl- or sec.-butyl chloride or the corresponding bromides, benzenesulfonates and p-toluenesulfonates, as well as ethylsulfate, diethylsulfate, butylsulfate, dibutylsulfate, sec.-butylsulfate and di-sec.-butylsulfate.

Specific examples of the phosphoramidothioates of the general formula (VI) include: O,O-diethyl-N-methyl-N-methanesulfonylphosphoramidothioate, O,O-diethyl-N-methyl-N-butanesulfonylphosphoramidothioate, O,O-diethyl-N-methyl-N-chloromethanesulfonylphosphoramidothioate, O,O-diethyl-N-methyl-N-benzenesulfonylphosphoramidothioate, O,O-diethyl-N-methyl-N-4-chlorobenzenesulfonylphosphoramidothioate, O,O-diethyl-N-2,5-dichlorobenzenesulfonylphosphoramidothioate, O,O-diethyl-N-methyl-N-2,5-dimethylbenzenesulfonylphosphoramidothioate, O,O-diethyl-N-methyl-N-2-nitrobenzenesulfonylphosphoramidothioate, O,O-diethyl-N-methyl-N-phenylmethanesulfonylphosphoramidothioate, O,O-diethyl-N-iso-propyl-N-methanesulfonylphosphoramidothioate, O,O-diethyl-N-allyl-N-methanesulfonylphosphoramidothioate, O,O-diethyl-N-allyl-N-benzenesulfonylphosphoramidothioate, O,O-diethyl-N-phenyl-N-methanesulfonylphosphoramidothioate, O,O-diethyl-N-2-tolyl-N-methanesulfonylphosphoramidothioate, and O,O-diethyl-N-4-chloro-2-tolyl-N-methylsulfonylphosphoramidothioate.

The dealkylating agents of the general formula (VIII) include, for instance, the following compounds: sodium hydrosulfide, potassium hydrosulfide, sodium methanethiolate, potassium ethanethiolate, sodium 2-propanethiolate, potassium methyl-xanthogenate, potassium ethylxanthogenate and ammonium sulfide.

Process variant (a) may be illustrated by the following equations:

(i) $(C_2H_5O)_2\overset{S}{\underset{\|}{P}}-N\overset{CH_3}{\underset{SO_2-\text{C}_6\text{H}_4-Cl}{\diagup}} + KSH \longrightarrow$ (ii) $\left[ \text{Cl}-\text{C}_6\text{H}_4-SO_2-\underset{CH_3}{N}-\overset{C_2H_5O}{\underset{S}{P}}\!\!=\!\!O \right].K + C_2H_5SH$ $\left[ \text{Cl}-\text{C}_6\text{H}_4-SO_2-\underset{CH_3}{N}-\overset{C_2H_5O}{\underset{S}{P}}\!\!=\!\!O \right].K + n\text{-}C_4H_9Br \longrightarrow$

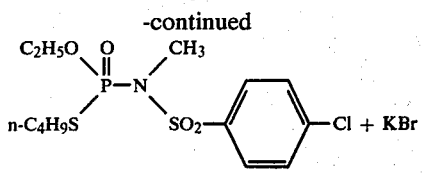

The potassium O-ethyl-N-methyl-N-4-chlorobenzenesulfonylphosphoramidothioate obtained in the first step can be isolated. However, it can successfully be alkylated in situ, that is without isolation, in order to obtain the intended product, O-ethyl-S-butyl-N-methyl-N-4-chlorobenzenesulfonylphosphoramidothiolate, in a high purity and in a high yield.

Process variant (a) of the present invention is carried out preferably using a solvent or diluent. Examples of such solvents or diluents are water and inert organic solvents selected from aliphatic, alicyclic and aromatic hydrocarbons, which optionally may be chlorinated, such as hexane, cyclohexane, petroleum ether, ligroin, benzene, toluene, xylene, methylene chloride, chloroform, carbon tetrachloride, ethylene chloride, trichloroethylene and chlorobenzene; ethers, such as diethyl ether, methyl ethyl ether, diisopropyl ether, dibutyl ether, propylene oxide, dioxane and tetrahydrofuran; ketones, such as acetone, methyl ethyl ketone, methyl isopropyl ketone and methyl isobutyl ketone; nitriles, such as acetonitrile, propionitrile and acrylonitrile; alcohols, such as methanol, ethanol, isopropanol, tert.-butanol and ethylene glycol; esters, such as ethyl acetate and amyl acetate; acid amides, and sulfoxides, such as dimethyl sulfoxide and dimethyl sulfone; and bases, such as pyridine.

Process variant (a) of the present invention can be performed in a wide temperature range. In general, the process is carried out at a temperature between $-20°$ C. and the boiling point of the mixture, preferably at a temperature of from $0°$ to $100°$ C. Furthermore, the reaction is carried out preferably at atmospheric pressure, although it can also be performed under an elevated or reduced pressure.

The thiophosphoryl halides of the general formula (IV) include, for instance, O,S-diethylthiophosphoryl chloride, O-ethyl-S-butylthiophosphoryl chloride and O-ethyl-S-sec.-butylthiophosphoryl chloride.

Examples of the salts represented by the general formula (V) are: sodium N-methylmethanesulfonamide, sodium N-methylbutanesulfonamide, sodium N-methylbenzenesulfonamide, sodium N-methyl-4-chlorobenzenesulfonamide, sodium N-methyl-2,5-dichlorobenzenesulfonamide, sodium N-methyl-2,5-dimethylbenzenesulfonamide, sodium N-methyl-2-nitrobenzenesulfonamide, sodium N-methyl-phenylmethanesulfonamide, sodium N-methylchloromethanesulfonamide, sodium N-isopropylmethanesulfonamide, sodium N-allylmethanesulfonamide, sodium N-allylbenzenesulfonamide, sodium benzenesulfonanilide, sodium methanesulfone-2-methylanilide, and sodium methanesulfone-4-chloro-2-methylanilide, and the corresponding potassium salts.

Process variant (b) may be illustrated by the following equation:

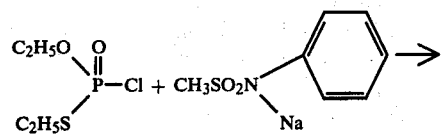
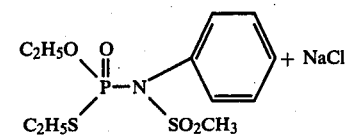

In carrying out process variant (b) an inert solvent or diluent is preferably used. The solvents mentioned above in connection with process variant (a) may be used to obtain the desired product in a high purity and in a high yield.

A wide range of temperature can be employed in process variant (b). Generally, the reaction is effected at a temperature between $-20°$ C. and the boiling point of the mixture, preferably at from $0°$ to $100°$ C. Although it is desirable for the reaction to be carried out at atmospheric pressure, it is also possible to perform the reaction under an elevated or reduced pressure.

As already mentioned, the compounds according to the present invention are distinguished by an excellent insecticidal, acaricidal and nematicidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine since they are also active against animal parasites, in particular ectoparasites such as parasitic fly larvae, spiders, ticks and nematodes.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the order of the *Thysanura*, for example *Lepisma saccharina;* from the order of the *Collembola*, for example *Onychiurus armatus;* from the order of *Orthoptera*, for example *Blatta orientalis, Periplaneta americana, Leucophaea maderae, Blattella germanica, Acheta domesticus, Gyrllotalpa* spp., *Locusta migratoria migratorioides, Melanoplus differentialis* and *Schistocerca gregaria;* from the order of the *Dermaptera*, for example *Forficula auricularia;* from the order of the *Isoptera*, for example *Reticulitermes* spp.;

from the order of the *Anoplura*, for example *Phylloxera vastatrix, Pemphigus* spp., *Pediculus humanus corporis, Haematopinus* spp. and *Linognathus* spp.;

from the order of the *Mallophaga*, for example *Trichodectes* spp. and *Damalinea* spp.;

from the order of the *Thysanoptera*, for example *Hercinothrips femoralis* and *Thrips tabaci*;

from the order of the *Heteroptera*, for example *Eurygaster* spp., *Dysdercus intermedius*, *Piesma quadrata*, *Cimex lectularious*, *Rhodnius prolixus* and *Triatoma* spp.;

from the order of the *Homoptera*, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

from the order of the *Lepidoptera*, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana*;

from the order of the *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica*;

from the order of the *Hymenoptera*, for example *Diprion* spp., *Hoplocampa* spp., *Lasius* spp., *Monomorium pharaonis* and *Vespa* spp.;

from the order of the *Diptera*, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp.,*Tannia* spp., *Bibio hortulanus, Oscinella frit, Phorbia* spp., *Pegomyia hyoscyami, Ceratitis capitata, Dacus oleae* and *Tipula paludosa*;

from the order of the *Siphonaptera*, for example *Xenopsylla cheopis* and *Ceratophyllus* spp.;

from the class of the *Arachnida*, for example *Scorpio maurus* and *Latrodectus mactans*;

from the order of the *Acarina*, for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp..

The plant-parasitic nematodes include *Pyratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphinema* spp., and *Trichodorus* spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e., plant compatible or herbicidally inert) pesticide diluents or extenders, i.e., diluents, carriers or extenders of the type usable in conventional pesticide formulations or compositions, e.g. conventional pesticide dispersible carrier vehicles such as gases, solutions, emulsions, wettable powders suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and methyl phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g. average particle diameter of from 50–100 microns, or even less, i.e., mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. arthropods and nematodes, which comprises applying to at least one of correspondingly (a) such arthropods, (b) such nematodes, and (c) the corresponding habitat thereof, i.e. the locus to be protected, e.g. to a growing crop, to an area where a crop is to be grown or to a domestic animal, a correspondingly combative or toxic amount, i.e., an arthropodicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The preparation of the new compounds of the present invention is illustrated, without limitation, by the following examples:

EXAMPLE 1

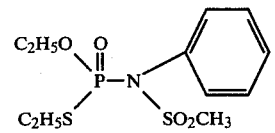

(1)

21.2 grams of sodium methanesulfonylanilide were dissolved in 100 ml of toluene, followed by the addition of 8.9 grams of O,S-diethyl-thiophosphoryl chloride. The resultant mixture was heated for 4 hours at 70° C. to complete the reaction. After the reaction, the product was cooled down to room temperature, washed with water and 1% aqueous sodium hydroxide and dried over anhydrous sodium sulfate. The toluene was distilled off under reduced pressure. The product was then distilled off at 75° C./1 mm Hg, thereby obtaining 22 grams, as a colorless oil, of O,S-diethyl-N-phenyl-N-methanesulfonylphosphoramidothiolate ($n_D^{20} = 1.5428$).

EXAMPLE 2

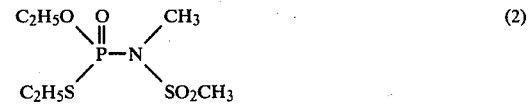

(2)

14.4 grams of sodium N-methylmethanesulfonylamide were suspended in 100 ml of acetonitrile. 18.9 grams of O,S-diethyl-thiophosphoryl chloride were added dropwise to the suspension at room temperature. After the addition, the mixture was heated for 3 hours at 35° to 40° C. That the reaction had been brought to completion was established by confirming the disappearance of the starting phosphoryl chloride by means of gas liquid chromatography.

The acetonitrile was distilled off from the reaction mixture under reduced pressure. The residue was mixed with benzene, washed with water and 1% aqueous sodium hydroxide and dried over anhydrous sodium sulfate. Benzene was removed by distillation. Further distillation was effected at 60° C./1 mm Hg in order to obtain 21 grams, as a colorless oil, of O,S-diethyl-N-methyl-N-methanesulfonylphosphoramidothiolate ($n_D^{20}=1.5042$).

EXAMPLE 3

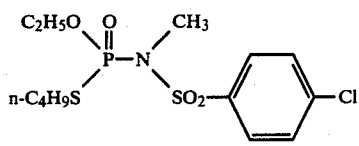
(3)

5.6 grams of potassium hydroxide were dissolved in 100 ml of ethanol and hydrogen sulfide gas was blown through the solution at room temperature to saturate it and to form an ethanolic solution of potassium hydrosulfide. To the resultant solution were added 35.7 grams of O,O-diethyl-N-methyl-N-4-chlorobenzenesulfonyl-phosphoramidothioate and the mixture was heated for 5 hours at 70° to 75° C. After lowering the internal temperature to about 50° C., 15 grams of n-butyl bromide were added to the mixture, followed by stirring and heating for 4 hours at 65° to 70° C. to complete the reaction. From the resulting mixture, low-boiling substances were evaporated off under reduced pressure, and toluene was added to the residue. The mixture was washed with water and 1% aqueous sodium hydroxide and again with water. After drying over anhydrous sodium sulfate, toluene was distilled off under reduced pressure to yield 25 grams, as a colorless oil, of O-ethyl-S-n-butyl-N-methyl-N-4-chlorobenzenesulfonylphosphoramidothiolate ($n_D^{20}=1.5252$).

EXAMPLE 4

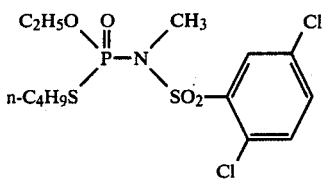
(4)

38 grams of sodium O-ethyl-N-methyl-N-2,5-dichlorobenzenesulfonylphosphoramidothioate were dissolved in 120 ml of methyl isobutyl ketone, and 15 grams of n-butyl bromide were added to the solution. The mixture was heated under stirring for 4 hours at 60° to 65° C. to complete the reaction. After cooling to room temperature the product was washed with 1% aqueous sodium hydroxide and water. After drying the product over anhydrous sodium sulfate, methyl isobutyl ketone was distilled off under reduced pressure to obtain 34 grams, as a slightly yellow viscous liquid, of O-ethyl-S-n-butyl-N-2,5-dichlorobenzenesulfonylphos-phoramidothiolate ($n_D^{20}=1.5372$):

The following compounds were prepared by methods analogous to those described above.

Table 1

$$\begin{array}{c} C_2H_5O \quad O \quad R^2 \\ \diagdown \parallel \diagup \\ P-N \\ \diagup \quad \diagdown \\ R^1S \quad SO_2R^3 \end{array} \quad (I)$$

| Compound No. | $R^1$ | $R^2$ | $R^3$ | Refractive index ($n_D^{20}$) |
|---|---|---|---|---|
| 5 | $C_2H_5$ | $C_3H_7$-iso | $CH_3$ | 1.5070 |
| 6 | $C_2H_5$ | $-CH_2CH=CH_2$ | $CH_3$ | 1.5120 |
| 7 | $C_2H_5$ | $2-CH_3-C_6H_4$ | $CH_3$ | 1.5417 |
| 8 | $C_2H_5$ | $2-CH_3-4-Cl-C_6H_3$ | $CH_3$ | 1.5442 |
| 9 | $C_2H_5$ | $CH_3$ | $CH_2Cl$ | 1.5088 |
| 10 | $n-C_4H_9$ | $CH_3$ | $n-C_4H_9$ | 1.4870 |
| 11 | $n-C_4H_9$ | $CH_3$ | $C_6H_5$ | 1.5155 |
| 12 | $n-C_4H_9$ | $CH_3$ | $2,5\text{-di-}CH_3-C_6H_3$ | 1.5293 |
| 13 | $n-C_4H_9$ | $CH_3$ | $2-NO_2-C_6H_4$ | 1.5351 |
| 14 | $n-C_4H_9$ | $CH_3$ | $-CH_2-C_6H_5$ | 1.5178 |
| 15 | $n-C_4H_9$ | $-CH_2CH=CH_2$ | $C_6H_5$ | 1.5272 |
| 16 | $sec.C_4H_9$ | $-CH_2CH=CH_2$ | $C_6H_5$ | 1.5268 |
| 17 | $n-C_4H_9$ | $CH_3$ | $CH_3$ | 1.4928 |
| 18 | $n-C_4H_9$ | $-CH_2CH=CH_2$ | $CH_3$ | 1.4960 |
| 19 | $n-C_4H_9$ | $C_6H_5$ | $CH_3$ | 1.5193 |

The compounds 6 and 10 to 19 were prepared using process variant (a); the compounds 5 and 7 to 9 were prepared using process variant (b).

Other compounds which can be similarly prepared include:

| Compound No. | $R^1$ | $R^2$ | $R^3$ |
|---|---|---|---|
| 20 | $C_2H_5$ | $CH_3$ $\mid$ $-CHCH=CH_2$ | $CH_3$ |
| 21 | $C_2H_5$ | $CH_3$ | $-CH_2-CH_2-CHBr-CH_2Br$ |
| 22 | $C_2H_5$ | $CH_3$ | $-CH_2CH_2-C_6H_5$ |

The superior activities of the novel compounds can be seen in the following comparative examples wherein the compounds according to the present invention are each identified by the number (given in brackets) from the foregoing preparative examples, while the known comparison compounds are identified as follows:

(A) = n-C₃H₇O     O
           \   ||
            P—NHSO₂CH₃
           /
       n-C₃H₇S (disclosed in U.S. Pat. No. 3,716,600)

(B) = n-C₃H₇O     O
           \   ||
            P—NHSO₂—⌬
           /
       n-C₃H₇S (disclosed in U.S. Pat. No. 3,716,600)

(C) =        O      CH₃
             ||    /
    (C₂H₅O)₂P—N
                  \
                   SO₂—⌬

(disclosed in Zh. Obsch. Khim., vol. 36, (5) 930)

(D) =        O      C₃H₇-iso
             ||    /
    (C₂H₅O)₂P—N
                  \
                   SO₂C₂H₅

(disclosed in British Patent Specification 833,863)

(E) =        O      C₂H₅
             ||    /
    (C₂H₅O)₂P—N
                  \
                   SO₂CH₃

(disclosed in British Patent Specification 833,863).

EXAMPLE 5

Test on larvae of Prodenia litura
Solvent: xylene, 3 parts by weight
Emulsifier: polyoxyethylene alkylphenyl ether, 1 part by weight To form a suitable preparation of the active compound, 1 part by weight of the active compound was mixed with the above amount of the solvent containing the above amount of the emulsifier, and the mixture was diluted with water to a predetermined concentration.

Sweet-potato leaves were dipped in an aqueous preparation, of a predetermined concentration, of the active compound. After drying in the air, the leaves were placed in a Petri dish 9 cm in diameter. Then, 10 third instar larvae of Prodenia litura Fabricius were placed in the Petri dish. The dish was placed in a constant-temperature room at 28° C. Twenty-four hours later, the number of dead larvae was determined in order to calculate the kill ratio. The results are shown in Table 2.

Table 2

Results of the test on the larvae of Prodenia litura

| Active compound | Kill Ratio (%) at a concentration of the active ingredient (ppm) | | |
|---|---|---|---|
|  | 1000 | 300 | 100 |
| (1) | 100 | 100 | 100 |
| (3) | 100 | 100 |  |
| (4) | 100 | 100 |  |
| (7) | 100 | 100 |  |
| (8) | 100 | 100 |  |
| (9) | 100 | 100 |  |
| (11) | 100 | 100 |  |
| (19) | 100 | 100 |  |
| (A) | 0 |  |  |
| (B) | 0 |  |  |
| (C) | 0 |  |  |
| (D) | 30 | 0 |  |
| (E) | 50 | 0 |  |

EXAMPLE 6

Test on Nephotettix cincticeps

Rice plants each about 10 cm in grass height were planted in pots each 12 cm in diameter. On to the rice plants there was applied an aqueous preparation, at a predetermined concentration, of the active compound (prepared as in Example 5) at a rate of 10 ml per pot. After drying the applied preparation, wire-gauze cages each 7 cm in diameter and 14 cm in height were placed over the pots, into which cages 30 female imagos of Nephotettix cincticeps were released. The pots were then placed in a constant-temperature room, and 24 hours later, the number of dead insects was determined in order to calculate the kill ratio. The results are shown in Table 3.

Table 3

Results of the test on Nephotettix cincticeps

| Active compound | Kill Ratio (%) at a concentration of the active ingredient (ppm) | |
|---|---|---|
|  | 1000 | 100 |
| (3) | 100 | 100 |
| (11) | 100 | 100 |
| (13) | 100 | 100 |
| (14) | 100 | 100 |
| (16) | 100 | 100 |
| (A) | 40 | 0 |
| (B) | 40 | 0 |
| (C) | 50 | 0 |
| (D) | 100 | 0 |
| (E) | 100 | 0 |

EXAMPLE 7

Test on the mite Tetranychus cinnabarinus (spray test)

The leaves of kidney bean plants in the two-leaf stage were infested with 50 to 60 larvae of Tetranychus cinnabarinus. The kidney bean plants were cultivated in pots each 9 cm in diameter. Two days after the infestation, an aqueous preparation, at a predetermined concentration, of the active compound (formulated as in Example 5) was sprayed over the leaves at a rate of 20 ml per pot. Then, the pots were put in a greenhouse. 10 days later, the acaricidal effect was evaluated and expressed on the following scale:

3—0% survival of the mites
2—not more than 5% survival
1—more than 5% survival up to 50% survival
0—more than 50% survival The results are shown in Table 4.

Table 4

Results of the test on Tetranychus cinnabarinus (Spray Test)

| Active compound | Acaricidal effect at a concentration of the active ingredient (ppm) of | | |
|---|---|---|---|
|  | 1000 | 300 | 100 |
| (1) | 3 | 3 | 3 |
| (2) | 3 | 3 | 2 |
| (3) | 3 | 3 | 3 |
| (4) | 3 | 3 | 3 |
| (5) | 3 | 3 | 3 |
| (6) | 3 | 3 | 3 |
| (7) | 3 | 3 | 3 |
| (8) | 3 | 3 | 3 |
| (10) | 3 | 3 | 3 |
| (12) | 3 | 3 | 3 |
| (13) | 3 | 3 | 3 |
| (14) | 3 | 3 | 3 |
| (15) | 3 | 3 | 3 |
| (16) | 3 | 3 | 3 |

Table 4-continued

| | Results of the test on *Tetranychus cinnabarinus* (Spray Test) | | |
|---|---|---|---|
| | Acaricidal effect at a concentration of the active ingredient (ppm) of | | |
| Active compound | 1000 | 300 | 100 |
| (17) | 3 | 3 | 2 |
| (18) | 3 | 3 | 3 |
| (19) | 3 | 3 | 3 |
| (A) | 0 | | |
| (B) | 0 | | |
| (C) | 0 | | |
| (D) | 0 | | |
| (E) | 0 | | |

EXAMPLE 8

Test on the mite *Tetranychus cinnabarinus* (irrigation test)

The leaves of kidney bean plants in the two-leaf stage were infested with 50 to 100 imagos of *Tetranychus cinnabarinus*.

Two days later, an aqueous preparation, at a predetermined concentration, of the active compound (formulated as in Example 5) was fed, by irrigation, to the roots of the kidney bean plants at a rate of 20 ml per pot. Then, the pots were placed in a greenhouse, and 10 days later, the acaricidal effect was evaluated and expressed on the following scale:

3—0% survival of the mites
2—not more than 5% survival
1—more than 5% survival up to 50% survival
0—more than 50% survival The results are shown in Table 5.

Table 5

| | Results of the test or *Tetranychus cinnabarinus* (Irrigation Test) | | |
|---|---|---|---|
| | Acaricidal effect at a concentration of the active ingredient (ppm) of | | |
| Active compound | 1000 | 300 | 100 |
| (1) | 3 | 3 | 3 |
| (2) | 3 | 3 | 3 |
| (5) | 3 | 3 | 3 |
| (6) | 3 | 3 | 3 |
| (7) | 3 | 3 | 3 |
| (17) | 3 | 3 | 3 |
| (A) | 0 | | |
| (B) | 0 | | |
| (C) | 0 | | |
| (D) | 0 | | |
| (E) | 0 | | |

EXAMPLE 9

Test on *Meloidogyne incognita acrita*

An active-compound preparation was prepared by pulverizing and mixing 2 parts by weight of the active compound and 98 parts by weight of talc.

The active compound processed as above was added to soil infested by *Meloidogyne incognita acrita* in such amounts as to give a concentration of 50 ppm, 25 ppm, 10 ppm and 5 ppm, respectively. The mixture was stirred and mixed uniformly and then charged into pots each of 0.0002 are. In the treated soil were sown about 20 seeds of tomato (variety: KURIHARA) per pot. The tomato seeds were cultivated in a greenhouse. Four weeks later, the grown roots were withdrawn without damaging them, and the degree of injury of 10 roots out of them was evaluated based on the following ratings to determine a root-knot index:

Degree of Injury

0—no root-knot formation (perfect control)
1—slight root-knot formation
3—much root-knot formation
4—most root-knot formation (corresponding to non-treatment)

$$\text{Root-knox index} = \Sigma \frac{(\text{rating} \times \text{number of individuals})}{(\text{total number of individuals examined})} \times 100$$

The evaluation was made in terms of the control effect in accordance with the following equation.

$$\text{Control effect} = \frac{(\text{Root-knot index of the untreated plot}) - (\text{Root-knot index of the treated plot})}{\text{Root-knot index of the untreated plot}} \times 100$$

A 100% control effect meant that the control was complete. The results are shown in Table 6.

Table 6

| | Results of the test on *Meloidogyne incognita acrita* | | | |
|---|---|---|---|---|
| | Control Effect (%) at a concentration of the active ingredient (ppm) of | | | |
| Active Compound | 50 | 25 | 10 | 5 |
| (1) | 100 | 100 | 100 | 100 |
| (2) | 100 | 100 | 100 | |
| (3) | 100 | 100 | | |
| (4) | 100 | 100 | | |
| (6) | 100 | 100 | 100 | |
| (9) | 100 | 100 | 100 | 100 |
| (11) | 100 | 100 | | |
| (A) | 0 | | | |
| (B) | 0 | | | |
| (C) | 0 | | | |
| (D) | 22.3 | | | |
| (E) | 22.3 | | | |

Other ways of formulating the compounds of the present invention are illustrated by the following examples.

EXAMPLE 10

A wettable powder was prepared by pulverizing and mixing 15 parts of compound No. 3, 80 parts of a mixture (1:5) of diatomaceous earth and kaolin, and 5 parts of an emulsifier (a polyoxyethylenealkyl phenyl ether). This could be diluted with water to 0.05% before application by spraying.

EXAMPLE 11

An emulsifiable concentrate was prepared by mixing and stirring 30 parts of compound No. 17, 30 parts of xylene, 30 parts of methylnaphthalene and 10 parts of a polyoxyethylene alkylphenyl ether. This could be diluted with water to 0.05% before spraying.

EXAMPLE 12

A dusting agent was prepared by pulverizing and mixing 2 parts of compound No. 9, and 98 parts of a mixture (1:3) of talc and clay. This could be applied by scattering.

EXAMPLE 13

A dusting agent was prepared by pulverizing and mixing 1.5 parts of compound No. 4, 0.5 part of isopropyl hydrogen phosphate (PAP), and 98 parts of a mixture (1:3) of talc and clay.

EXAMPLE 14

10 parts of compound No. 1, 10 parts of bentonite, 78 parts of a mixture (1:3) of talc and clay, and 2 parts of lignin sulfonate were mixed. 25 parts of water were added to the mixture. The whole was mixed thoroughly and then processed with an extrusion granulator into granules of 20 to 40 mesh, which were dried at 40°–50° C.

EXAMPLE 15

95 parts of clay powder having a particle size distribution of 0.2 to 2 mm were placed in a rotary mixer. During rotation, there were sprayed over the particles 5 parts of a solution of compound No. 2 in an organic solvent, thereby wetting them uniformly. Then, drying at 40° to 50° C. was effected in order to form granules.

EXAMPLE 16

An oil preparation was prepared by mixing and stirring 0.5 part of compound No. 6, 20 parts of a high boiling aromatic compound and 79.5 parts of kerosine.

It will be appreciated that the instant specification and claims are set forth by way of illustration and not limitation, and that various modifications and changes may be made without departing from the spirit and scope of the present invention.

What is claimed is:

1. An O-alkyl-S-alkyl-N-sulfonylphosphoramidothiolate of the formula $$\begin{array}{c} C_2H_5O \\ \diagdown \\ R^1S \end{array} \overset{O}{\underset{\|}{P}} - N \begin{array}{c} R^2 \\ \diagup \\ \diagdown \\ SO_2R^3 \end{array}$$

in which
  $R^1$ is ethyl, n-butyl or sec.-butyl,
  $R^2$ is alkyl with 1–6 carbon atoms, alkenyl with 2–6 carbon atoms, phenyl substituted with up to two substituents selected from the group consisting of halogen and alkyl with 1–6 carbon atoms, and
  $R^3$ is alkyl or halogen-substituted alkyl with 1–6 carbon atoms, aralkyl, phenyl or phenyl substituted with up to two substituents selected from the group consisting of halogen, alkyl with 1–6 carbon atoms and nitro.

2. A method of combating arthropods or nematodes, which comprises applying to the arthropods or nematodes, or to a habitat thereof, an arthropodicidally or nematicidally effective amount of a compound according to claim 1.

3. A compound according to claim 1, in which
  $R^2$ is alkyl with 1–4 carbon atoms, alkenyl with 2–4 carbon atoms, phenyl or phenyl substituted with up to two substituents selected from the group consisting of chlorine and methyl, and
  $R^3$ is alkyl or haloalkyl with 1–4 carbon atoms, benzyl, 2-phenylethyl, phenyl or phenyl substituted with up to two substituents selected from the group consisting of methyl, nitro and chlorine.

4. A compound according to claim 1, wherein the compound is O,S-diethyl-N-methyl-N-methanesulfonylphosphoramidothiolate of the formula $$\begin{array}{c} C_2H_5O \\ \diagdown \\ C_2H_5S \end{array} \overset{O}{\underset{\|}{P}} - N \begin{array}{c} CH_3 \\ \diagup \\ \diagdown \\ SO_2CH_3 \end{array}$$

5. A compound according to claim 1, wherein the compound is O-ethyl-S-n-butyl-N-methyl-N-4-chlorobenzenesulfonylphosphoramidothiolate of the formula $$\begin{array}{c} C_2H_5O \\ \diagdown \\ n\text{-}C_4H_9S \end{array} \overset{O}{\underset{\|}{P}} - N \begin{array}{c} CH_3 \\ \diagup \\ \diagdown \\ SO_2\text{-}\!\!\!\bigcirc\!\!\!\text{-}Cl \end{array}$$

6. A compound according to claim 1, wherein the compound is O,S-diethyl-N-isopropyl-N-methanesulfonylphosphoramidothiolate of the formula $$\begin{array}{c} C_2H_5O \\ \diagdown \\ C_2H_5S \end{array} \overset{O}{\underset{\|}{P}} - N \begin{array}{c} C_3H_7\text{-}iso \\ \diagup \\ \diagdown \\ SO_2CH_3 \end{array}$$

7. A compound according to claim 1, wherein the compound is O,S-diethyl-N-allyl-N-methanesulfonylphosphoramidothiolate of the formula $$\begin{array}{c} C_2H_5O \\ \diagdown \\ C_2H_5S \end{array} \overset{O}{\underset{\|}{P}} - N \begin{array}{c} CH_2CH=CH_2 \\ \diagup \\ \diagdown \\ SO_2CH_3 \end{array}$$

8. A compound according to claim 1, wherein the compound is O,S-diethyl-N-2-tolyl-N-methanesulfonylphosphoramidothiolate of the formula $$\begin{array}{c} C_2H_5O \\ \diagdown \\ C_2H_5S \end{array} \overset{O}{\underset{\|}{P}} - N \begin{array}{c} \bigcirc\!\!\!\text{-}CH_3 \\ \diagdown \\ SO_2CH_3 \end{array}$$

9. A compound according to claim 1, wherein the compound is O,S-diethyl-N-phenyl-N-methane-sulfonylphosphoramidothiolate of the formula $$\begin{array}{c} C_2H_5O \\ \diagdown \\ C_2H_5S \end{array} \overset{O}{\underset{\|}{P}} - N \begin{array}{c} \bigcirc \\ \diagdown \\ SO_2CH_3 \end{array}$$

10. A compound according to claim 1, wherein the compound is O-ethyl-S-n-butyl-N-methyl-N-2,5-dichlorobenzenesulfonylphosphoramidothiolate of the formula

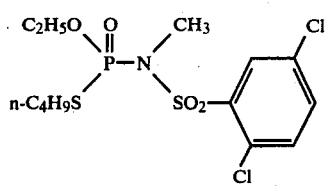

11. An arthropodicidal or nematicidal composition containing as active ingredient an arthropodicidally or nematicidally effective amount of a compound according to claim 1 in admixture with a diluent.

12. The method according to claim 2 in which said compound is

O,S-diethyl-N-methyl-N-methanesulfonylphosphoramidothiolate,
O-ethyl-S-n-butyl-N-methyl-N-4-chlorobenzenesulfonylphosphoramidothiolate,
O,S-diethyl-N-isopropyl-N-methanesulfonylphosphoramidothiolate,
O,S-diethyl-N-allyl-N-methanesulfonylphosphoramidothiolate,
O,S-diethyl-N-2-tolyl-N-methanesulfonylphosphoramidothiolate,
O,S-diethyl-N-phenyl-N-methanesulfonylphosphoramidothiolate, or
O-ethyl-S-n-butyl-N-methyl-N-2,5-dichlorobenzenesulfonylphosphoramidothiolate.

* * * * *